US009919017B2

(12) United States Patent
Yamaguchi et al.

(10) Patent No.: US 9,919,017 B2
(45) Date of Patent: Mar. 20, 2018

(54) BIOLOGICALLY ACTIVE SUBSTANCE-CONTAINING WATER-SOLUBILIZING PREPARATION AND METHOD FOR PRODUCING THE SAME

(75) Inventors: Takao Yamaguchi, Hyogo (JP); Toshinori Ikehara, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 13/982,841

(22) PCT Filed: Jan. 31, 2012

(86) PCT No.: PCT/JP2012/052133
§ 371 (c)(1),
(2), (4) Date: Jul. 31, 2013

(87) PCT Pub. No.: WO2012/105551
PCT Pub. Date: Aug. 9, 2012

(65) Prior Publication Data
US 2013/0309338 A1   Nov. 21, 2013

(30) Foreign Application Priority Data

Feb. 1, 2011 (JP) .................................. 2011-019892

(51) Int. Cl.
| | |
|---|---|
| *A61K 36/484* | (2006.01) |
| *A61K 47/14* | (2017.01) |
| *A61K 36/287* | (2006.01) |
| *A61K 9/00* | (2006.01) |
| *A61K 9/08* | (2006.01) |

(52) U.S. Cl.
CPC .......... *A61K 36/484* (2013.01); *A61K 9/0095* (2013.01); *A61K 9/08* (2013.01); *A61K 36/287* (2013.01); *A61K 47/14* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 5,990,180 A | 11/1999 | Shioguchi et al. | |
| 2005/0118289 A1 | 6/2005 | Ikehara et al. | |
| 2006/0073176 A1 | 4/2006 | Segawa et al. | |
| 2006/0134085 A1 | 6/2006 | Yamaguchi et al. | |
| 2008/0131515 A1* | 6/2008 | Ogawa et al. | ................ 424/489 |
| 2009/0087419 A1 | 4/2009 | Sakai et al. | |
| 2009/0208472 A1 | 8/2009 | Sakai et al. | |

FOREIGN PATENT DOCUMENTS

| | | |
|---|---|---|
| CN | 1642565 A | 7/2005 |
| JP | 02-204417 | 8/1990 |
| JP | 8-323189 | 12/1996 |
| JP | 2001-081039 A | 3/2001 |
| JP | 2003-176233 A | 6/2003 |
| JP | 2004091392 A * | 3/2004 |
| JP | 3528382 B2 | 5/2004 |
| JP | 2004-196781 A | 7/2004 |
| JP | 2004-261005 A | 9/2004 |
| JP | 2005-143317 A | 6/2005 |
| JP | 3653884 B2 | 6/2005 |
| JP | 2005-343799 A | 12/2005 |
| WO | WO-03/084556 A1 | 10/2003 |
| WO | WO-2007/097412 A1 | 8/2007 |
| WO | WO-2007/123044 A1 | 11/2007 |
| WO | WO-2008/004509 A1 | 1/2008 |

OTHER PUBLICATIONS

"Diglycerol monooleate". Internet Archive Date: Nov. 7, 2007. [Retrieved from the internet on: Aug. 4, 2015]. Retrieved from: <URL: https://web.archive.org/web/20071107125621/http://www.chemicalland21.com/lifescience/uh/DIGLYCERY%20MONOOLEATE.htm>.*
International Search Report issued in PCT/JP2012/052133 dated May 1, 2012.
Office Action dated Jun. 13, 2014 in Chinese Application No. 201280007293.5.
Mexican Office Action with English Translation issued in Application No. MX/a/2013/008090 received Nov. 7, 2016.

* cited by examiner

*Primary Examiner* — Amy L Clark
(74) *Attorney, Agent, or Firm* — Polsinelli PC

(57) ABSTRACT

An object of the present invention is to provide a water-solubilizing preparation that is obtained by convenient steps without use of a special apparatus such as a high-pressure homogenizer, does not impair the original properties of a water-based material even after being added to the material, has high dispersibility and transparency and excellent heat resistance and acid resistance, and can maintain stability. The water-solubilizing preparation of the present invention is a biologically active substance-containing water-solubilizing preparation comprising 1 to 50% by weight of an oily ingredient (A) containing a biologically active substance and oil, 10 to 98% by weight of a polyglycerin fatty acid ester (B) having an HLB value of 12.5 or larger, and 1 to 40% by weight of a surfactant (C) having an HLB value of 7 to 11.8.

22 Claims, No Drawings

BIOLOGICALLY ACTIVE SUBSTANCE-CONTAINING WATER-SOLUBILIZING PREPARATION AND METHOD FOR PRODUCING THE SAME

CROSS REFERENCE TO RELATED APPLICATIONS

This application is a National Phase filing under 35 U.S.C. § 371 of PCT/JP2012/052133 filed on Jan. 31, 2012; and this application claims priority to Application No. 2011-019892 filed in Japan on Feb. 1, 2011 under 35 U.S.C. § 119; the entire contents of all are hereby incorporated by reference.

TECHNICAL FIELD

The present invention relates to a biologically active substance-containing water-solubilizing preparation that can be used in, for example, foods or drinks such as health foods and foods with health claims (foods for specified health use and foods with nutrient function claims), pharmaceutical drugs, quasi drugs, or cosmetics, and a method for producing the same.

BACKGROUND ART

Biologically active substances, when being lipid-soluble, may be barely added to foods such as drinks in many cases. For example, a hydrophobic licorice component that is extracted from licorice or a residue of water extraction of licorice using an organic solvent or the like has been confirmed to exhibit many useful effects such as an antioxidative effect, an antibacterial effect, an enzyme inhibitory effect, an antitumor effect, an antiallergic effect, and an antiviral effect. Nevertheless, this hydrophobic licorice component is not dissolved in water and cannot be readily added directly to water-based foods. In addition, the hydrophobic licorice component is barely dissolved in general oils. Furthermore, this component in the form of an organic solvent extract is used with difficulties due to its instability such as easy consolidation or coloring.

Thus, for example, Patent Literature 1 employs a method involving mixing a hydrophobic licorice extract with a fat-based solvent containing 10% or more of an oil-soluble polyhydric alcohol fatty acid ester. This hydrophobic licorice component-containing fat composition, however, cannot be solubilized directly in a water-based material or the like.

Patent Literature 2 discloses that a hydrophobic flavonoid of licorice dissolved in medium-chain fatty acid triglyceride is prepared into an oil-in-water emulsion in the presence of an emulsifier. This technique, however, is merely directed to water dispersibility and is not aimed at transparency or acid resistance.

Patent Literature 3 proposes a composition containing an oily extract of licorice and polyglycerin lauric acid ester. Its acid resistance or heat resistance, which is required for addition to drinks, is not sufficient.

Patent Literature 4 discloses a licorice polyphenol-containing oil-in-water emulsion composition containing a polyglycerin fatty acid ester composed of a fatty acid residue having 14 or more carbon atoms. Its production requires a homogenization treatment under high-pressure conditions of 50 MPa or higher.

Patent Literature 5 discloses a fat-solubilized composition comprising a polyglycerin having an average degree of polymerization of 6 to 10 and a monoester of saturated fatty acid having 12 to 14 carbon atoms. Its production requires a homogenization treatment under high-pressure conditions of 135 MPa or higher.

Patent Literature 6 discloses an oil-soluble substance-solubilized composition comprising a polyglycerin having an average degree of polymerization of 5 to 10 and a monoester of myristic acid or oleic acid. Its production requires a homogenization treatment under high-pressure conditions of 100 MPa or higher.

Patent Literature 7 discloses a self-emulsifying preparation comprising polyoxyethylene sorbitan fatty acid ester. This preparation reportedly forms a microemulsion upon contact with an aqueous medium. Use of the polyoxyethylene sorbitan fatty acid ester in foods, however, is strictly limited in Japan or other countries. Thus, this preparation cannot be applied to a wide range of foods.

Patent Literature 8 discloses a stable aqueous composition containing an oil-soluble substance solubilized or dispersed in a water-soluble medium using a special polyglycerin saturated fatty acid ester having a clouding point of 20° C. or higher.

CITATION LIST

Patent Literature

Patent Literature 1: WO03/084556
Patent Literature 2: JP Patent Publication (Kokai) No. 2-204417 A (1990)
Patent Literature 3: JP Patent Publication (Kokai) No. 2003-176233 A (2003)
Patent Literature 4: WO2007/097412
Patent Literature 5: JP Patent No. 3528382
Patent Literature 6: JP Patent No. 3653884
Patent Literature 7: WO2007/123044
Patent Literature 8: JP Patent Publication (Kokai) No. 8-323189 A (1996)

SUMMARY OF INVENTION

Technical Problem

As mentioned above, the conventional techniques are applied only in a limited way for intended use in water-based materials, due to, for example, poor dispersibility or transparency, insufficiency of heat resistance or acid resistance required particularly for health drinks or the like, or the need for using a special surfactant. In addition, the general preparation of an oil-in-water emulsion composition using a polyglycerin fatty acid ester often requires a high-pressure treatment and thus disadvantageously involves complicated steps. An object of the present invention is to provide a water-solubilizing preparation that is obtained by convenient steps, does not impair the original properties of a water-based material even after being added to the material, and further maintains high stability even under acidic conditions.

Solution to Problem

In view of the present circumstances, the present inventors have conducted diligent studies and consequently found that: a stable water-solubilizing preparation can be easily prepared by a combination of particular surfactants differing in hydrophile-lipophile balance (HLB) value; and the obtained water-solubilizing preparation is also a self-emulsifying preparation that forms a microemulsion merely upon contact with an aqueous medium. On the basis of these findings, the present invention has been completed.

Specifically, the present invention relates to a biologically active substance-containing water-solubilizing preparation comprising 1 to 50% by weight of an oily ingredient (A) containing a biologically active substance and oil, 10 to 98% by weight of a polyglycerin fatty acid ester (B) having an HLB value of 12.5 or larger, and 1 to 40% by weight of a surfactant (C) having an HLB value of 7 to 11.8.

The present invention also relates to a method for producing a biologically active substance-solubilized aqueous solution, comprising adding a biologically active substance-containing water-solubilizing preparation to an aqueous medium (water-based solvent) such as water or an aqueous solution and then heat-treating and/or acid-treating the mixture, the biologically active substance-containing water-solubilizing preparation comprising 1 to 50% by weight of an oily ingredient (A) containing a biologically active substance and oil, 10 to 98% by weight of a polyglycerin fatty acid ester (B) having an HLB value of 12.5 or larger, and 1 to 40% by weight of a surfactant (C) having an HLB value of 7 to 11.8.

The present specification encompasses the contents described in the specification of Japanese Patent Application No. 2011-019892 on which the priority of the present application is based.

Advantageous Effects of Invention

The biologically active substance-containing water-solubilizing preparation of the present invention can be produced as a stable water-solubilizing preparation with a high concentration that allows a lipid-soluble biologically active substance to be solubilized in water without the need of complicated steps such as a high-pressure treatment. The biologically active substance-containing water-solubilizing preparation of the present invention can also be easily diffused in an aqueous medium to form a microemulsion excellent in acid resistance and heat resistance. The obtained microemulsion has high storage stability. Accordingly, the aqueous emulsion obtained from the biologically active substance-containing water-solubilizing preparation of the present invention has excellent acid resistance and heat resistance and as such, is applicable to various uses.

DESCRIPTION OF EMBODIMENTS

Hereinafter, the present invention will be described specifically.

The biologically active substance-containing water-solubilizing preparation of the present invention (hereinafter, also simply referred to as the "water-solubilizing preparation of the present invention") is a preparation comprising 1 to 50% by weight of an oily ingredient (A) containing a biologically active substance and oil, 10 to 98% by weight of a polyglycerin fatty acid ester (B) having an HLB value of 12.5 or larger, and 1 to 40% by weight of a surfactant (C) having an HLB value of 7 to 11.8.

The biologically active substance used in the oily ingredient (A) in the water-solubilizing preparation of the present invention is not particularly limited as long as the substance is lipid-soluble or poorly water-soluble and has biological activity. Preferable examples thereof include a plant extract, a fat-soluble vitamin, and a carotenoid.

The plant extract is not particularly limited, and a hydrophobic plant extract that is obtained by extraction from a general edible plant using an organic solvent can be used.

The plant extract is a hydrophobic extract that is obtained by extraction using an organic solvent such as ethanol, acetone, or hexane from a plant (also including processed products of the plant) selected from, for example, licorice, chrysanthemum flower, turmeric, perilla, clove, cinnamon, ginger, lemon grass, peppermint, *Houttuynia cordata*, coicis semen, rice bran, cornflower, fennel, Chinese matrimony vine, *Zanthoxylum piperitum, Patrinia triloba* var. *palmata, Dioscorea rhizome, Sparganium stoloniferum* Buch-Ham, *Tinospora capillipes* Gagnep, *Gynostemma pentaphyllum, Biota orientalis* L., *Pulsatilla cernua*, parsley, onion, nutmeg, wild rice, gluten feed, Konjac Tobiko (powder blown off in the process of grinding dried *Amorphophallus konjac*), bell pepper, horseradish, lemon, hot pepper, sesame, spearmint, marigold, *Haematococcus algae*, and *Brassica juncea* var. *integrifolia*. The plant extract contains, for example, a polyphenol and/or a terpene as an active ingredient. Among them, the plant extract is preferably an extract of licorice or chrysanthemum flower, more preferably a hydrophobic extract of licorice or chrysanthemum flower, further preferably an extract that is obtained by extraction with an ethanol from licorice or chrysanthemum flower, i.e., an ethanol extract of licorice or an ethanol extract of chrysanthemum flower.

Examples of the fat-soluble vitamin include, but not particularly limited to, vitamin A, vitamin D, vitamin E (tocopherol, tocotrienol, etc.), vitamin K, coenzyme Q (an oxidized form of coenzyme Q10, a reduced form of coenzyme Q10, etc.), and their derivatives. Of course, any mixture of these fat-soluble vitamins may be used.

Examples of the carotenoid include, but not particularly limited to, carotenes, xanthophylls, and their derivatives. Examples of the carotenes include α carotene, β carotene, γ carotene, δ carotene, ε carotene, and lycopene. The xanthophylls are preferably lutein, zeaxanthin, canthaxanthin, fucoxanthin, antheraxanthin, violaxanthin, astaxanthin, and the like.

In the water-solubilizing preparation of the present invention, the biologically active substance as described above is mixed with oil, and this mixture is used as the oily ingredient (A). In this context, preferably, the mixture of the biologically active substance and the oil is visually uniformly mixed.

The oil used in the oily ingredient (A) is not particularly limited and may be, for example, a natural oil or fat from an animal or a plant or may be synthetic or processed oil. The oil or fat is more preferably oil or fat that is acceptable for foods, cosmetics, or pharmaceuticals. Specific examples thereof can include: plant oils such as coconut oil, palm oil, palm kernel oil, linseed oil, camellia oil, rice germ oil, rapeseed oil, rice oil, peanut oil, corn oil, wheat germ oil, soybean oil, perilla oil, cottonseed oil, sunflower seed oil, kapok oil, evening primrose oil, shea butter, sal butter, cocoa butter, sesame oil, safflower oil, olive oil, pomegranate oil, and Goya oil; animal fats such as lard, milk fat, fish oil, and beef tallow; medium-chain fatty acid triglyceride (MCT) having 6 to 12 carbon atoms, preferably 8 to 12 carbon atoms, in each fatty acid; oils (e.g., hardened oil) processed therefrom by fractionation, hydrogenation, transesterification, etc.; and partial glycerides thereof. Needless to say, any mixture of these oils may be used. Particularly, in the case of using a plant extract as the biologically active substance, medium-chain fatty acid triglyceride is most preferred in terms of its ability to efficiently dissolve the plant extract as well as easy handleability, oxidation stability, etc.

In the water-solubilizing preparation of the present invention, the mixing ratio of the biologically active substance and the oil in the oily ingredient (A) is appropriately selected depending on the properties of the biologically active substance and the type of the oil used. In the case of using, for example, an ethanol extract of licorice or an ethanol extract of chrysanthemum flower as the biologically active substance and medium-chain fatty acid triglyceride as the oil, the composition of the oily ingredient (A) is preferably a ratio of 50 to 90% by weight of the medium-chain fatty acid triglyceride to 10 to 50% by weight of the ethanol extract of licorice or the ethanol extract of chrysanthemum flower, more preferably a ratio of 60 to 80% by weight of the medium-chain fatty acid triglyceride to 20 to 40% by weight of the ethanol extract of licorice or the ethanol extract of chrysanthemum flower.

The content of the oily ingredient (A) containing the biologically active substance in the biologically active substance-containing water-solubilizing preparation (water-solubilizing preparation of the present invention) is not particularly limited as long as the content falls within the range of 1 to 50% by weight. The content is preferably in the range of 1 to 40% by weight, more preferably 5 to 30% by weight, most preferably 10 to 30% by weight. A water-solubilizing preparation of the present invention containing the oily ingredient (A) at a content less than 1% by weight needs to be ingested in large amounts for orally administering a predetermined amount of the biologically active substance. By contrast, a preparation containing the oily ingredient (A) at a content of 50% by weight or more has stability insufficient for addition to an aqueous medium.

The polyglycerin fatty acid ester (B) used in the water-solubilizing preparation of the present invention is not particularly limited as long as the polyglycerin fatty acid ester has an HLB value of 12.5 or larger. The polyglycerin fatty acid ester (B) is preferably a polyglycerin fatty acid ester having an average degree of glycerin polymerization of 6 or larger, more preferably a polyglycerin fatty acid ester having an average degree of polymerization of 6 to 10, further preferably decaglycerin fatty acid ester having an average degree of polymerization of 10. Likewise, the fatty acid constituting the polyglycerin fatty acid ester (B) is not particularly limited and is preferably a fatty acid having 8 to 20 carbon atoms, more preferably a fatty acid having 10 to 18 carbon atoms, further preferably a fatty acid having 12 to 16 carbon atoms, particularly preferably a fatty acid having 12 or 14 carbon atoms, i.e., lauric acid or myristic acid. Also, the polyglycerin fatty acid ester (B) may be in the form of monoester or polyester and is preferably in the form of monoester or diester, more preferably polyglycerin monofatty acid ester, which is in the form of a monoester. Specifically, preferable examples of the polyglycerin fatty acid ester (B) include decaglycerin monolauric acid ester, decaglycerin monomyristic acid ester, decaglycerin monostearic acid ester, decaglycerin monooleic acid ester, and decaglycerin monocaprylic acid ester. Among them, decaglycerin monolauric acid ester or decaglycerin monomyristic acid ester is particularly preferred.

The content of the polyglycerin fatty acid ester (B) having an HLB value of 12.5 or larger in the water-solubilizing preparation of the present invention is not particularly limited as long as the content falls within the range of 10 to 98% by weight. The content is preferably in the range of 35 to 98% by weight, more preferably 60 to 92% by weight, most preferably 60 to 85% by weight. A water-solubilizing preparation of the present invention containing the polyglycerin fatty acid ester (B) at a content less than 10% by weight fails to uniformly diffuse therein the ingredients, which in turn repel each other. By contrast, a preparation containing the polyglycerin fatty acid ester (B) at a content more than 98% by weight has stability insufficient for addition to an aqueous medium.

The surfactant (C) used in the water-solubilizing preparation of the present invention is not particularly limited as long as the surfactant has an HLB value of 7 to 11.8. For example, a polyglycerin fatty acid ester, a sucrose fatty acid ester, a sorbitan fatty acid ester, a polyoxyethylene sorbitan fatty acid ester, or a lecithin can be used. Among them, a polyglycerin fatty acid ester is preferred, and a polyglycerin fatty acid ester having an average degree of glycerin polymerization of 2 to 6 is more preferred. The fatty acid constituting the polyglycerin fatty acid ester used as the surfactant (C) is not particularly limited and may be selected usually from fatty acids having 6 to 22 carbon atoms. The fatty acid is preferably a fatty acid having 10 to 18 carbon atoms, more preferably a fatty acid having 12 to 18 carbon atoms, further preferably oleic acid or stearic acid, most preferably oleic acid. Specifically, the surfactant (C) may be preferably selected from diglycerin monooleic acid ester, diglycerin monostearic acid ester, triglycerin monooleic acid ester, triglycerin monostearic acid ester, tetraglycerin monolauric acid ester, tetraglycerin monooleic acid ester, tetraglycerin monostearic acid ester, pentaglycerin monooleic acid ester, pentaglycerin dioleic acid ester, pentaglycerin trioleic acid ester, pentaglycerin monostearic acid ester, pentaglycerin distearic acid ester, pentaglycerin tristearic acid ester, hexaglycerin monooleic acid ester, hexaglycerin dioleic acid ester, hexaglycerin trioleic acid ester, hexaglycerin tetraoleic acid ester, hexaglycerin monostearic acid ester, hexaglycerin distearic acid ester, hexaglycerin tristearic acid ester, hexaglycerin tetrastearic acid ester, and the like, each of which has an HLB value of 7 to 11.8. Among them, diglycerin monooleic acid ester or hexaglycerin monooleic acid ester is particularly preferred.

The content of the surfactant (C) having an HLB value of 7 to 11.8 in the water-solubilizing preparation of the present invention is not particularly limited as long as the content falls within the range of 1 to 40% by weight. The content is preferably in the range of 1 to 25% by weight, more preferably 3 to 10% by weight, most preferably 5 to 10% by weight. A water-solubilizing preparation containing the surfactant (C) at a content less than 1% by weight has stability insufficient for addition to an aqueous medium. By contrast, a preparation containing the surfactant (C) at a content more than 40% by weight fails to uniformly diffuse therein the ingredients, which in turn repel each other.

The water-solubilizing preparation of the present invention can be easily prepared merely by uniformly mixing the oily ingredient (A) containing a biologically active substance and oil, the polyglycerin fatty acid ester (B) having an HLB value of 12.5 or larger, and the surfactant (C) having an HLB value of 7 to 11.8. Specifically, these ingredients are each heated, if necessary, and need only to be mixed mechanically or manually. Thus, the water-solubilizing preparation of the present invention can be produced even without the need of a special stirring apparatus for the mixing. In other words, the production of the water-solubilizing preparation of the present invention does not require an emulsifying machine that applied a strong shear force, a pressurizing emulsifying machine such as a high-pressure homogenizer, or the like. Of course, these apparatuses may be used.

The range of pressure for the mixing is not particularly limited. Since the present invention does not require high-pressure emulsification, 100 kgf/cm$^2$ (approximately 10 MPa) or lower usually suffices. Of course, the mixing may be carried out without pressure application (i.e., under normal pressure (approximately 0.1 MPa)).

The order of addition of each ingredient for the mixing or its addition method is not particularly limited, and the desired biologically active substance-containing water-solubilizing preparation can be prepared even by any order of addition and any addition method.

The step of preparing the water-solubilizing preparation of the present invention is preferably performed under temperature conditions that can secure the flowability of each added ingredient to some extent, from the viewpoint of production efficiency. This step is carried out in the range of usually 30 to 100° C., preferably 40 to 90° C., more preferably 50 to 80° C.

Also from the viewpoint of securing flowability during mixing, water and/or an alcohol may be added, for the mixing, as an ingredient other than the oily ingredient (A) containing a biologically active substance and oil, the polyglycerin fatty acid ester (B) having an HLB value of 12.5 or larger, and the surfactant (C) having an HLB value of 7 to 11.8. The water-solubilizing preparation of the present invention further comprising a certain amount of water and/or an alcohol can have a reduced viscosity and is thus particularly advantageous for industrial production. The content of the water or the alcohol or the total content of the water and the alcohol that can be added to the water-solubilizing preparation of the present invention is not particularly limited. The upper limit thereof is preferably 12% by weight or less, more preferably 10% by weight or less, particularly preferably 8% by weight or less. A (total) content of the water and/or the alcohol exceeding 12% by weight tends to reduce the stability of a biologically active substance-solubilized aqueous solution obtained by adding the water-solubilizing preparation of the present invention to an aqueous medium. By contrast, a larger content of water may disadvantageously cause the need of hygienic management during the storage of the biologically active substance-containing water-solubilizing preparation. The lower limit of the (total) content of the water and/or the alcohol in the water-solubilizing preparation of the present invention is not particularly limited. Since the water-solubilizing preparation of the present invention does not necessarily require this water and/or alcohol, the lower limit thereof is 0% by weight. The water and/or the alcohol are added in an amount of usually 1% by weight or more, preferably 2% by weight or more, more preferably 3% by weight or more, for the purpose of improving the flowability or reducing the viscosity. In this context, the water that is added thereto is not particularly limited, and, for example, distilled water, deionized water, or drinking water can be used. Also, the alcohol that is added thereto is not particularly limited, and ethanol can be used preferably because the subsequent step of removing the alcohol is not necessarily required. The addition of ethanol is also preferred because it enhances the properties of the resulting water-solubilizing preparation as mentioned later. By contrast, it may not be preferred that the added alcohol should remain in the water-solubilizing preparation, depending on its type or the intended use of the preparation. In such a case, after the mixing step, the alcohol can be partially distilled off until an acceptable amount by, for example, concentration under reduced pressure, or can be completely removed.

The water-solubilizing preparation of the present invention has favorable solubility in water. Thus, the water-solubilizing preparation of the present invention can be mixed with an aqueous medium to thereby easily prepare a biologically active substance-solubilized aqueous solution in which a biologically active substance is solubilized. Particularly, when ethanol added in the step of producing the water-solubilizing preparation of the present invention remains in the water-solubilizing preparation, this water-solubilizing preparation has particularly favorable solubility in an aqueous solvent. Thus, use of the water-solubilizing preparation can prepare a highly transparent biologically active substance-solubilized aqueous solution. In this context, the biologically active substance-solubilized aqueous solution also includes the forms of microemulsions and oil-in-water emulsion compositions such as nanoemulsions.

The water-solubilizing preparation of the present invention comprises the oily ingredient (A), the polyglycerin fatty acid ester (B) having an HLB value of 12.5 or larger, the surfactant (C) having an HLB value of 7 to 11.8, and the water and/or the alcohol that are added if necessary and can further contain, for example, a dye, an aggregation inhibitor, an absorption promoter, a thickener, a stabilizer (polysaccharide thickeners, etc.), a solubilizer, a pH adjuster, an antioxidant, and a flavor, without particular limitations.

Water itself or an aqueous solution containing a water-soluble component dissolved in water is preferably used as the aqueous medium that is miscible with the water-solubilizing preparation of the present invention. However, the biologically active substance-solubilized aqueous solution containing the water-solubilizing preparation of the present invention dissolved in water is not encompassed by the aqueous solution used in this context.

Examples of the water-soluble component that can be dissolved in the aqueous medium include, but not particularly limited to: water-soluble vitamins such as vitamin C; organic acids such as citric acid, acetic acid, and malic acid; and other components such as amino acids, peptides, L-carnitine, various salts, caffeine, fruit juices, milk constituents, tea extracts, and coffee extracts. Alternatively, the water-soluble component may be a polyhydric alcohol. Examples of the polyhydric alcohol include saccharides such as monosaccharide, disaccharide, oligosaccharide, and liquid sugar syrup, and sugar alcohols such as glycerin and sorbitol. Any of these water-soluble components can be added to the aqueous medium without influencing emulsification.

For preparing the biologically active substance-solubilized aqueous solution using the water-solubilizing preparation of the present invention, the upper limit of the amount of the biologically active substance-containing water-solubilizing preparation added is not particularly limited. From the viewpoint of the versatility of the resulting biologically active substance-solubilized aqueous solution, 20 g or lower, preferably 10 g or lower, more preferably 5 g or lower of the water-solubilizing preparation of the present invention is usually mixed with 100 mL of the aqueous medium such as water or an aqueous solution. The biologically active substance-containing water-solubilizing preparation (water-solubilizing preparation of the present invention) added in an amount of 20 g or higher may not be uniformly diffused, resulting in difficult-to-handle properties. Likewise, the lower limit of the amount of the water-solubilizing preparation of the present invention added is not particularly limited. From the viewpoint of an effective amount of the biologically active substance contained in the resulting biologically active substance-solubilized aqueous solution, 10 mg or higher, preferably 30 mg or higher, more preferably 50 mg or higher of the water-solubilizing preparation of the present invention is usually mixed with 100 mL of the aqueous medium such as water.

The water-solubilizing preparation of the present invention has high solubility in water and as such, is usually easily dissolved or emulsified merely by stirring with an impeller-type stirrer (a magnetic stirrer, a propeller-type stirrer, an axial-flow turbine-type stirrer, a radial turbine-type stirrer, an anchor-type stirrer, etc.) when uniformly mixed into the aqueous medium such as water or an aqueous solution. The emulsification does not particularly require using an emulsifying machine known in the art, such as a stirring homomixer or a high-pressure homogenizer and may be stabilized by such a high-pressure emulsification or homogenization treatment.

The biologically active substance-solubilized aqueous solution prepared using the water-solubilizing preparation of the present invention is excellent in heat resistance and acid resistance and is suitable for use that requires acid resistance or heat resistance, for example, application to health drinks, etc. Even if the biologically active substance-solubilized aqueous solution has insufficient transparency or dispersibility, its dispersibility or transparency can also be improved by a heat treatment or an acid treatment, particularly, a heat treatment. From such a viewpoint, one aspect of the present invention also provides a method for producing a biologically active substance-solubilized aqueous solution, comprising adding a biologically active substance-containing water-solubilizing preparation to water or an aqueous solution and then heat-treating and/or acid-treating the mixture, the biologically active substance-containing water-solubilizing preparation comprising 1 to 50% by weight of an oily ingredient (A) containing a biologically active substance and oil, 10 to 98% by weight of a polyglycerin fatty acid ester (B) having an HLB value of 12.5 or larger, and 1 to 40% by weight of a surfactant (C) having an HLB value of 7 to 11.8. In the case of performing the heat treatment, conditions such as a heating temperature are not particularly limited. The water-solubilizing preparation of the present invention is mixed with the aqueous medium, and then, the mixed solution is usually heated to 80° C. or higher, preferably 85° C. or higher, more preferably 90° C. or higher, to thereby improve dispersibility or transparency. Alternatively, in the case of performing the acid treatment, acidity is usually pH 5.0 or lower, preferably pH 4.0 or lower, more preferably pH 3.0 or lower. In this context, the acidity is generally adjusted by a method which usually involves adding an acidic substance to the mixed solution of the water-solubilizing preparation of the present invention and the aqueous medium and adjusting the pH of the obtained biologically active substance-solubilized aqueous solution to a predetermined value. The acidic substance that is added thereto needs to be selected according to the intended use of the biologically active substance-solubilized aqueous solution. For example, the biologically active substance-solubilized aqueous solution for use in drinks requires using an acidic substance that is acceptable as a food additive (acetic acid, malic acid, ascorbic acid, citric acid, sorbic acid, carbon dioxide, etc.).

The biologically active substance-containing water-solubilizing preparation obtained in the present invention has favorable solubility in water and as such, may be dissolved in the aqueous medium such as water, as described above, and used in the form of a biologically active substance-solubilized aqueous solution in health drinks or cosmetics or may be mixed directly with general foods, feed, or the like. In this way, the water-solubilizing preparation of the present invention can be used in foods such as general foods, foods with nutrient function claims, foods for specified health use, nutritional supplements, nutritional products, and drinks; pharmaceutical drugs such as therapeutic drugs, preventive drugs, and drugs for animals; cosmetics; feed; etc.

EXAMPLES

Next, the present invention will be described in more detail with reference to Examples. However, the present invention is not intended to be limited to these Examples.

Example 1

20 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 74 parts by weight of decaglycerin monomyristic acid ester (manufactured by Mitsubishi-Kagaku Foods Corp.; trade name "M-7D", HLB=15) as the polyglycerin fatty acid ester (B), and 6 parts by weight of pentaglycerin trioleic acid ester (manufactured by Taiyo Kagaku Co., Ltd.; trade name "Sunsoft A-173E", HLB=7.0) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 2

20 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 74 parts by weight of decaglycerin monomyristic acid ester (manufactured by Mitsubishi-Kagaku Foods Corp.; trade name "M-7D", HLB=15) as the polyglycerin fatty acid ester (B), and 6 parts by weight of diglycerin monooleic acid ester (manufactured by Riken Vitamin Co., Ltd.; trade name "DO-100V", HLB=7.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 3

20 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 74 parts by weight of decaglycerin monomyristic acid ester (manufactured by Mitsubishi-Kagaku Foods Corp.; trade name "M-7D", HLB=15) as the polyglycerin fatty acid ester (B), 6 parts by weight of diglycerin monooleic acid ester (manufactured by Riken Vitamin Co., Ltd.; trade name "DO-100V", HLB=7.4) as the surfactant (C), and further, 500 parts by weight of ethanol were uniformly mixed at 200 rpm at room temperature under normal pressure using a stirrer (manufactured by AS ONE Corp.; trade name "Tornado PM202"). The obtained mixed solution was concentrated under reduced pressure. The ethanol was distilled off until the ethanol content reached 12.1% by weight to obtain a biologically active substance-containing water-solubilizing preparation.

Example 4

20 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 74 parts by weight of decaglycerin monomyristic acid ester (manufactured by Mitsubishi-Kagaku Foods Corp.; trade name "M-7D", HLB=15) as the polyglycerin fatty acid ester (B), and 6 parts by weight of tetraglycerin monolauric acid ester (manufactured by Sakamoto Yakuhin Kogyo Co., Ltd.; trade name "SY-Glyster ML-310", HLB=10.3) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 5

20 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 74 parts by weight of decaglycerin monomyristic acid ester (manufactured by Mitsubishi-Kagaku Foods Corp.; trade name "M-7D", HLB=15) as the polyglycerin fatty acid ester (B), and 6 parts by weight of tetraglycerin monostearic acid ester (manufactured by Sakamoto Yakuhin Kogyo Co., Ltd.; trade name "SY-Glyster MS-3S", HLB=8.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 6

20 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 74 parts by weight of decaglycerin monomyristic acid ester (manufactured by Mitsubishi-Kagaku Foods Corp.; trade name "M-7D", HLB=15) as the polyglycerin fatty acid ester (B), and 6 parts by weight of hexaglycerin monooleic acid ester (manufactured by Sakamoto Yakuhin Kogyo Co., Ltd.; trade name "SY-Glyster MO-5 S", HLB=11.6) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Comparative Example 1

20 parts by weight of oil containing an ethanol extract of licorice (manufactured by Kaneka Corp.; trade name "Glavonoid", MCT=70% by weight, ethanol extract of licorice=30% by weight), 74 parts by weight of decaglycerin monomyristic acid ester (manufactured by Mitsubishi-Kagaku Foods Corp.; trade name "M-7D", HLB=15), and 6 parts by weight of decaglycerin monostearic acid ester (manufactured by Sakamoto Yakuhin Kogyo Co., Ltd.; trade name "SY-Glyster MM-750", HLB=15.5) were each heated to 50° C. and uniformly mixed at 200 rpm under normal pressure using a stirrer (manufactured by AS ONE Corp.; trade name "Tornado PM202") to obtain a biologically active substance-containing composition.

Comparative Example 2

20 parts by weight of oil containing an ethanol extract of licorice (manufactured by Kaneka Corp.; trade name "Glavonoid", MCT=70% by weight, ethanol extract of licorice=30% by weight), 74 parts by weight of decaglycerin monomyristic acid ester (manufactured by Mitsubishi-Kagaku Foods Corp.; trade name "M-7D", HLB=15), and 6 parts by weight of decaglycerin monostearic acid ester (manufactured by Taiyo Kagaku Co., Ltd.; trade name "Sunsoft Q-18S", HLB=12.0) were each heated to 50° C. and uniformly mixed at 200 rpm under normal pressure using a stirrer (manufactured by AS ONE Corp.; trade name "Tornado PM202") to obtain a biologically active substance-containing composition.

Comparative Example 3

20 parts by weight of oil containing an ethanol extract of licorice (manufactured by Kaneka Corp.; trade name "Glavonoid", MCT=70% by weight, ethanol extract of licorice=30% by weight), 6 parts by weight of diglycerin mono/di-oleic acid ester (manufactured by Taiyo Kagaku Co., Ltd.; trade name "Sunsoft Q-17B", HLB=6.5), and 6 parts by weight of diglycerin monooleic acid ester diglycerin mono/dioleic acid ester (manufactured by Taiyo Kagaku Co., Ltd.; trade name "Sunsoft Q-17B", HLB=6.5) were each heated to 50° C. and uniformly mixed at 200 rpm under normal pressure using a stirrer (manufactured by AS ONE Corp.; trade name "Tornado PM202") to obtain a biologically active substance-containing composition.

Comparative Example 4

20 parts by weight of oil containing an ethanol extract of licorice (manufactured by Kaneka Corp.; trade name "Glavonoid", MCT=70% by weight, ethanol extract of licorice=30% by weight), 74 parts by weight of hexaglycerin monooleic acid ester (manufactured by Sakamoto Yakuhin Kogyo Co., Ltd.; trade name "SY-Glyster MO-5S", HLB=11.6), and 6 parts by weight of diglycerin monooleic acid ester (manufactured by Riken Vitamin Co., Ltd.; trade name "DO-100V", HLB=7.4) were each heated to 50° C. and uniformly mixed at 200 rpm under normal pressure using a stirrer (manufactured by AS ONE Corp.; trade name "Tornado PM202") to obtain a biologically active substance-containing composition.

Example 7

1.5 g each of the biologically active substance-containing water-solubilizing preparations obtained in Examples 1 to 6 and the biologically active substance-containing compositions obtained in Comparative Examples 1 to 4 was added into 100 mL of distilled water and uniformly diffused to obtain a biologically active substance-solubilized aqueous solution or an aqueous solution of the biologically active substance-containing composition. The pH of this biologically active substance-solubilized aqueous solution or aqueous solution of the biologically active substance-containing composition was adjusted to 2.9 by the addition of a small amount of citric acid thereinto to prepare an acid-treated solution. The particle size distribution of the obtained acid-treated solution was measured using a dynamic light scattering particle size distribution analyzer (manufactured by Horiba Ltd.; trade name "LB-550"). The analysis results are shown in Table 1. This acid-treated solution was heated until the internal temperature reached 95° C. to prepare an acid/heat-treated solution. Likewise, the particle size distribution of the obtained acid/heat-treated solution was measured using a dynamic light scattering particle size distribution analyzer (manufactured by Horiba Ltd.; trade name "LB-550"). The analysis results are shown in Table 1.

TABLE 1

| Test agent used | Particle size distribution of acid-treated solution (median size) (nm) | Particle size distribution of acid/heat-treated solution (median size) (nm) |
| --- | --- | --- |
| Water-solubilizing preparation of Example 1 | 346.0 | 82.7 |
| Water-solubilizing preparation of Example 2 | 119.8 | 35.8 |
| Water-solubilizing preparation of Example 3 | 25.1 | 37.7 |
| Water-solubilizing preparation of Example 4 | 347.0 | 50.4 |
| Water-solubilizing preparation of Example 5 | 795.4 | 36.5 |
| Water-solubilizing preparation of Example 6 | 152.6 | 25.1 |
| Composition of Comparative Example 1 | 504.9 | 518.8 |
| Composition of Comparative Example 2 | 388.1 | 116.4 |
| Composition of Comparative Example 3 | 355.1 | 274.9 |
| Composition of Comparative Example 4 | 275.6 | Oil out (immeasurable) |

Example 8

27 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 67 parts by weight of decaglycerin monomyristic acid ester (manufactured by Mitsubishi-Kagaku Foods Corp.; trade name "M-7D", HLB=15) as the polyglycerin fatty acid ester (B), and 6 parts by weight of diglycerin monooleic acid ester (manufactured by Riken Vitamin Co., Ltd.; trade name "DO-100V", HLB=7.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 9

27 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 67 parts by weight of decaglycerin monomyristic acid ester (manufactured by Mitsubishi-Kagaku Foods Corp.; trade name "M-7D", HLB=15) as the polyglycerin fatty acid ester (B), and 6 parts by weight of tetraglycerin monolauric acid ester (manufactured by Sakamoto Yakuhin Kogyo Co., Ltd.; trade name "SY-Glyster ML-310", HLB=10.3) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 10

27 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 67 parts by weight of decaglycerin monomyristic acid ester (manufactured by Mitsubishi-Kagaku Foods Corp.; trade name "M-7D", HLB=15) as the polyglycerin fatty acid ester (B), and 6 parts by weight of hexaglycerin monooleic acid ester (manufactured by Sakamoto Yakuhin Kogyo Co., Ltd.; trade name "SY-Glyster MO-5 S", HLB=11.6) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 11

27 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 67 parts by weight of decaglycerin monomyristic acid ester (manufactured by Mitsubishi-Kagaku Foods Corp.; trade name "M-7D", HLB=15) as the polyglycerin fatty acid ester (B), and 6 parts by weight of hexaglycerin distearic acid ester (manufactured by Sakamoto Yakuhin Kogyo Co., Ltd.; trade name "SY-Glyster MS-5S", HLB=11.6) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Comparative Example 5

27 parts by weight of oil containing an ethanol extract of licorice (manufactured by Kaneka Corp.; trade name "Glavonoid", MCT=70% by weight, ethanol extract of licorice=30% by weight), 67 parts by weight of hexaglycerin monooleic acid ester (manufactured by Sakamoto Yakuhin Kogyo Co., Ltd.; trade name "SY-Glyster MO-5S", HLB=11.6), and 6 parts by weight of diglycerin monooleic acid ester (manufactured by Riken Vitamin Co., Ltd.; trade name "DO-100V", HLB=7.4) were each heated to 50° C. and uniformly mixed at 200 rpm under normal pressure using a stirrer (manufactured by AS ONE Corp.; trade name "Tornado PM202") to obtain a biologically active substance-containing composition.

Example 12

1.11 g each of the biologically active substance-containing water-solubilizing preparations obtained in Examples 8 to 11 and the biologically active substance-containing composition obtained in Comparative Example 5 was added into 100 mL of distilled water and uniformly diffused to obtain a biologically active substance-solubilized aqueous solution or an aqueous solution of the biologically active substance-containing composition. The pH of this biologically active substance-solubilized aqueous solution or aqueous solution of the biologically active substance-containing composition was adjusted to 2.9 by the addition of a small amount of citric acid thereinto to prepare an acid-treated solution. The particle size distribution of the obtained acid-treated solution was measured using a dynamic light scattering particle size distribution analyzer (manufactured by Horiba Ltd.; trade name "LB-550"). The analysis results are shown in Table 2. This acid-treated solution was heated until the internal temperature reached 95° C. to prepare an acid/heat-treated solution. Likewise, the particle size distribution of the obtained acid/heat-treated solution was measured using a dynamic light scattering particle size distribution analyzer (manufactured by Horiba Ltd.; trade name "LB-550"). The analysis results are shown in Table 2.

TABLE 2

| Test agent used | Particle size distribution of acid-treated solution (median size) (nm) | Particle size distribution of acid/heat-treated solution (median size) (nm) |
| --- | --- | --- |
| Water-solubilizing preparation of Example 8 | 92.7 | 35.4 |
| Water-solubilizing preparation of Example 9 | 166.8 | 25.6 |
| Water-solubilizing preparation of Example 10 | 136.2 | 27.7 |
| Water-solubilizing preparation of Example 11 | 443.2 | 26.7 |
| Composition of Comparative Example 5 | 505.1 | Oil out (immeasurable) |

Example 13

With respect to 27 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, decaglycerin monomyristic acid ester (manufactured by Mitsubishi-Kagaku Foods Corp.; trade name "M-7D", HLB=15) as the polyglycerin fatty acid ester (B) and diglycerin monooleic acid ester (manufactured by Riken Vitamin Co., Ltd.; trade name "DO-100V", HLB=7.4) as the surfactant (C) were each used at a ratio shown in Table 3. These three ingredients were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

1.11 g of the obtained biologically active substance-containing water-solubilizing preparation was added into 100 mL of distilled water and uniformly diffused to obtain a biologically active substance-solubilized aqueous solution. The pH of this biologically active substance-solubilized aqueous solution was adjusted to 2.9 by the addition of a small amount of citric acid thereinto. Then, the resulting solution was heated until the internal temperature reached 95° C. to prepare an acid/heat-treated solution. The particle size distribution of the obtained acid/heat-treated solution was measured using a dynamic light scattering particle size distribution analyzer (manufactured by Horiba Ltd.; trade name "LB-550"). The analysis results are shown in Table 3.

TABLE 3

| | Decaglycerin monomyristic acid ester: HLB15 (part by weight) | Diglycerin monooleic acid ester: HLB7.4 (part by weight) | Particle size distribution (median size) (nm) |
| --- | --- | --- | --- |
| Example 13 | 70 | 3 | 131.4 |
| | 67 | 6 | 35.4 |
| | 63 | 10 | 144.1 |
| | 48 | 25 | 230.4 |
| | 37 | 36 | 227.9 |
| Comparative Example 6 | 73 | 0 | (558)* |
| Comparative Example 7 | 6 | 67 | 2839.8 |

*Many large oil droplets exceeding the measurement range (6000 nm or lower) were present.

Comparative Example 6

27 parts by weight of oil containing an ethanol extract of licorice (manufactured by Kaneka Corp.; trade name "Glavonoid", MCT=70% by weight, ethanol extract of licorice=30% by weight) and 73 parts by weight of decaglycerin monomyristic acid ester (manufactured by Mitsubishi-Kagaku Foods Corp.; trade name "M-7D", HLB=15) were each heated to 50° C. and uniformly mixed at 200 rpm under normal pressure using a stirrer (manufactured by AS ONE Corp.; trade name "Tornado PM202") to obtain a biologically active substance-containing composition.

1.11 g of the obtained biologically active substance-containing composition was added into 100 mL of distilled water and uniformly diffused to obtain an aqueous solution of the biologically active substance-containing composition. The pH of this aqueous solution of the biologically active substance-containing composition was adjusted to 2.9 by the addition of a small amount of citric acid thereinto. Then, the resulting solution was heated until the internal temperature reached 95° C. to prepare an acid/heat-treated solution. The particle size distribution of the obtained acid/heat-treated solution was measured using a dynamic light scattering particle size distribution analyzer (manufactured by Horiba Ltd.; trade name "LB-550"). The analysis results are shown in Table 3.

Comparative Example 7

27 parts by weight of oil containing an ethanol extract of licorice (manufactured by Kaneka Corp.; trade name "Glavonoid", MCT=70% by weight, ethanol extract of licorice=30% by weight), 6 parts by weight of decaglycerin monomyristic acid ester (manufactured by Mitsubishi-Kagaku Foods Corp.; trade name "M-7D", HLB=15), and 67 parts by weight of diglycerin monooleic acid ester (manufactured by Riken Vitamin Co., Ltd.; trade name "DO-100V", HLB=7.4) were each heated to 50° C. and uniformly mixed at 200 rpm under normal pressure using a stirrer (manufactured by AS ONE Corp.; trade name "Tornado PM202") to obtain a biologically active substance-containing composition.

1.11 g of the obtained biologically active substance-containing composition was added into 100 mL of distilled water and uniformly diffused to obtain an aqueous solution of the biologically active substance-containing composition. The pH of this aqueous solution of the biologically active substance-containing composition was adjusted to 2.9 by the addition of a small amount of citric acid thereinto. Then, the resulting solution was heated until the internal temperature reached 95° C. to prepare an acid/heat-treated solution. The particle size distribution of the obtained acid/heat-treated solution was measured using a dynamic light scattering particle size distribution analyzer (manufactured by Horiba Ltd.; trade name "LB-550"). The analysis results are shown in Table 3.

Production Example 1

A chrysanthemum flower head was infiltrated for 3 hours with a 93% aqueous ethanol solution heated to 50° C. to perform extraction. Then, the residue was removed by filtration to obtain an extracted solution. The obtained extracted solution was concentrated under reduced pressure for removal of the solvent to obtain an ethanol extract of chrysanthemum flower.

Example 14

2.8 parts by weight of MCT was added to 1 part by weight of the ethanol extract of chrysanthemum flower obtained in Production Example 1 to prepare oil containing an ethanol extract of chrysanthemum flower.
20.5 parts by weight of the oil containing an ethanol extract of chrysanthemum flower as the oily ingredient (A) containing a biologically active substance and oil, 64 parts by weight of decaglycerin monolauric acid ester (manufactured by Riken Vitamin Co., Ltd.; trade name "J-0021", HLB=16) as the polyglycerin fatty acid ester (B), and 9.5 parts by weight of diglycerin monooleic acid ester (manufactured by Riken Vitamin Co., Ltd.; trade name "DO-100V", HLB=7.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 15

2.8 parts by weight of MCT was added to 1 part by weight of the ethanol extract of chrysanthemum flower obtained in Production Example 1 to prepare oil containing an ethanol extract of chrysanthemum flower.
20.5 parts by weight of the oil containing an ethanol extract of chrysanthemum flower as the oily ingredient (A) containing a biologically active substance and oil, 64 parts by weight of decaglycerin monomyristic acid ester (manufactured by Mitsubishi-Kagaku Foods Corp.; trade name "M-7D", HLB=15) as the polyglycerin fatty acid ester (B), and 9.5 parts by weight of diglycerin monooleic acid ester (manufactured by Riken Vitamin Co., Ltd.; trade name "DO-100V", HLB=7.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 16

2.8 parts by weight of MCT was added to 1 part by weight of the ethanol extract of chrysanthemum flower obtained in Production Example 1 to prepare oil containing an ethanol extract of chrysanthemum flower.
13.7 parts by weight of the oil containing an ethanol extract of chrysanthemum flower as the oily ingredient (A) containing a biologically active substance and oil, 74 parts by weight of decaglycerin monolauric acid ester (manufactured by Riken Vitamin Co., Ltd.; trade name "J-0021", HLB=16) as the polyglycerin fatty acid ester (B), and 6.3 parts by weight of diglycerin monooleic acid ester (manufactured by Riken Vitamin Co., Ltd.; trade name "DO-100V", HLB=7.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 17

2.8 parts by weight of MCT was added to 1 part by weight of the ethanol extract of chrysanthemum flower obtained in Production Example 1 to prepare oil containing an ethanol extract of chrysanthemum flower.
13.7 parts by weight of the oil containing an ethanol extract of chrysanthemum flower as the oily ingredient (A) containing a biologically active substance and oil, 74 parts by weight of decaglycerin monomyristic acid ester (manufactured by Mitsubishi-Kagaku Foods Corp.; trade name "M-7D", HLB=15) as the polyglycerin fatty acid ester (B), and 6.3 parts by weight of diglycerin monooleic acid ester (manufactured by Riken Vitamin Co., Ltd.; trade name "DO-100V", HLB=7.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 18

2.8 parts by weight of MCT was added to 1 part by weight of the ethanol extract of chrysanthemum flower obtained in Production Example 1 to prepare oil containing an ethanol extract of chrysanthemum flower.
13.7 parts by weight of the oil containing an ethanol extract of chrysanthemum flower as the oily ingredient (A) containing a biologically active substance and oil, 74 parts by weight of decaglycerin monomyristic acid ester (manufactured by Mitsubishi-Kagaku Foods Corp.; trade name "M-7D", HLB=15) as the polyglycerin fatty acid ester (B), 6.3 parts by weight of diglycerin monooleic acid ester (manufactured by Riken Vitamin Co., Ltd.; trade name "DO-100V", HLB=7.4) as the surfactant (C), and 500 parts by weight of ethanol were added and uniformly mixed at 200 rpm at room temperature under normal pressure using a stirrer (manufactured by AS ONE Corp.; trade name "Tornado PM202"). The obtained mixed solution was concentrated under reduced pressure. The ethanol was distilled off until the ethanol content reached 11.5% to obtain a biologically active substance-containing water-solubilizing preparation.

Example 19

3.3 g each of the biologically active substance-containing water-solubilizing preparations obtained in Examples 14 and 15 or 5.0 g each of the biologically active substance-containing water-solubilizing preparations obtained in Examples 16 to 18 was added into 100 mL of distilled water and uniformly diffused to obtain a biologically active substance-solubilized aqueous solution. The pH of this biologically active substance-solubilized aqueous solution was adjusted to 2.9 by the addition of a small amount of citric acid. Then, the resulting solution was heated until the internal temperature reached 95° C. to prepare an acid/heat-treated solution. The particle size distribution of the obtained acid/heat-treated solution was measured using a dynamic light scattering particle size distribution analyzer (manufactured by Horiba Ltd.; trade name "LB-550"). The analysis results are shown in Table 4.

TABLE 4

| Test agent used | Particle size distribution of acid/heat-treated solution (median size) (nm) |
|---|---|
| Water-solubilizing preparation of Example 14 | 18.9 |
| Water-solubilizing preparation of Example 15 | 29.2 |
| Water-solubilizing preparation of Example 16 | 19.6 |
| Water-solubilizing preparation of Example 17 | 24.2 |
| Water-solubilizing preparation of Example 18 | 22.9 |

Example 20

2.8 parts by weight of MCT was added to 1 part by weight of the ethanol extract of chrysanthemum flower obtained in Production Example 1 to prepare oil containing an ethanol extract of chrysanthemum flower.

17.1 parts by weight of the oil containing an ethanol extract of chrysanthemum flower as the oily ingredient (A) containing a biologically active substance and oil, 69 parts by weight of decaglycerin monolauric acid ester (manufactured by Riken Vitamin Co., Ltd.; trade name "J-0021", HLB=16) as the polyglycerin fatty acid ester (B), and 7.9 parts by weight of diglycerin monooleic acid ester (manufactured by Riken Vitamin Co., Ltd.; trade name "DO-100V", HLB=7.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 21

2.8 parts by weight of MCT was added to 1 part by weight of the ethanol extract of chrysanthemum flower obtained in Production Example 1 to prepare oil containing an ethanol extract of chrysanthemum flower.

17.1 parts by weight of the oil containing an ethanol extract of chrysanthemum flower as the oily ingredient (A) containing a biologically active substance and oil, 69 parts by weight of decaglycerin monomyristic acid ester (manufactured by Mitsubishi-Kagaku Foods Corp.; trade name "M-7D", HLB=15) as the polyglycerin fatty acid ester (B), and 7.9 parts by weight of diglycerin monooleic acid ester (manufactured by Riken Vitamin Co., Ltd.; trade name "DO-100V", HLB=7.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

Example 22

4.0 g each of the biologically active substance-containing water-solubilizing preparations obtained in Examples 20 and 21 was added into 100 mL of distilled water and uniformly diffused to obtain a biologically active substance-solubilized aqueous solution. This biologically active substance-solubilized aqueous solution was heated until the internal temperature reached 95° C. to prepare a heat-treated solution. The particle size distribution of the heat-treated solution was measured using a dynamic light scattering particle size distribution analyzer (manufactured by Horiba Ltd.; trade name "LB-550"). The analysis results are shown in Table 5.

TABLE 5

| Test agent used | Particle size distribution of heat-treated solution (median size) (nm) |
|---|---|
| Water-solubilizing preparation of Example 20 | 17.4 |
| Water-solubilizing preparation of Example 21 | 25.9 |

Example 23

(Drink Evaluation 1)

The biologically active substance-containing water-solubilizing preparations of Examples 8 and 9 were used. Each drink sample was prepared according to a recipe shown below and heated until the internal temperature reached 95° C. to sterilize the sample. All the obtained drink samples were in a clear state without causing oiling attributed to heating.

| Biologically active substance-containing water-solubilizing preparation | 1.05 parts by weight |
|---|---|
| Sucrose | 4.71 parts by weight |
| Water | 94.24 parts by weight |
| Citric acid | pH was adjusted to 2.9. |

Example 24

(Drink Evaluation 2)

The biologically active substance-containing water-solubilizing preparations of Examples 20 and 21 were used. Each drink sample was prepared according to a recipe shown below and heated until the internal temperature reached 95° C. to sterilize the sample. All the obtained drink samples were in a clear state without causing oiling attributed to heating.

| Biologically active substance-containing water-solubilizing preparation | 1.05 parts by weight |
|---|---|
| Sucrose | 4.71 parts by weight |
| Water | 94.24 parts by weight |
| Citric acid | pH was adjusted to 2.9. |

Example 25

27 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 62 parts by weight of decaglycerin monomyristic acid ester (manufactured by Mitsubishi-Kagaku Foods Corp.; trade name "M-7D", HLB=15) as the polyglycerin fatty acid ester (B), 6 parts by weight of diglycerin monooleic acid ester (manufactured by Riken Vitamin Co., Ltd.; trade name "DO-100V", HLB=7.4) as the surfactant (C), and 5 parts by weight of distilled water were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

1.11 g of the obtained biologically active substance-containing water-solubilizing preparation was added into 100 mL of distilled water and uniformly diffused to obtain a biologically active substance-solubilized aqueous solution. The pH of this biologically active substance-solubilized aqueous solution was adjusted to 2.9 by the addition of a small amount of citric acid thereinto. Then, the resulting solution was heated until the internal temperature reached 95° C. to prepare an acid/heat-treated solution. The particle size distribution of the obtained acid/heat-treated solution was measured immediately after its preparation and after 19-day storage at 25° C. using a dynamic light scattering particle size distribution analyzer (manufactured by Horiba Ltd.; trade name "LB-550"). The analysis results are shown in Table 6.

TABLE 6

| Test agent used | Particle size distribution of acid/heat-treated solution (median size) (nm) | |
| --- | --- | --- |
| | Immediately after preparation | After 19-day storage at 25° C. |
| Water-solubilizing preparation of Example 25 | 38.5 | 82.5 |
| Water-solubilizing preparation of Example 26 | 56.1 | 120.1 |

Example 26

27 parts by weight of oil containing an ethanol extract of licorice (manufactured by Kaneka Corp.; trade name "Glavonoid", MCT=70% by weight, ethanol extract of licorice=30% by weight) as the oily ingredient (A) containing a biologically active substance and oil, 57 parts by weight of decaglycerin monomyristic acid ester (manufactured by Mitsubishi-Kagaku Foods Corp.; trade name "M-7D", HLB=15) as the polyglycerin fatty acid ester (B), 6 parts by weight of diglycerin monooleic acid ester (manufactured by Riken Vitamin Co., Ltd.; trade name "DO-100V", HLB=7.4) as the surfactant (C), and 10 parts by weight of distilled water were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

1.11 g of the obtained biologically active substance-containing water-solubilizing preparation was added into 100 mL of distilled water and uniformly diffused to obtain a biologically active substance-solubilized aqueous solution. The pH of this biologically active substance-solubilized aqueous solution was adjusted to 2.9 by the addition of a small amount of citric acid thereinto. Then, the resulting solution was heated until the internal temperature reached 95° C. to prepare an acid/heat-treated solution. The particle size distribution of the obtained acid/heat-treated solution was measured immediately after its preparation and after 19-day storage at 25° C. using a dynamic light scattering particle size distribution analyzer (manufactured by Horiba Ltd.; trade name "LB-550"). The analysis results are shown in Table 6.

Example 27

2.8 parts by weight of MCT was added to 1 part by weight of the ethanol extract of chrysanthemum flower obtained in Production Example 1 to prepare oil containing an ethanol extract of chrysanthemum flower.

20.5 parts by weight of the oil containing an ethanol extract of chrysanthemum flower as the oily ingredient (A) containing a biologically active substance and oil, 68 parts by weight of decaglycerin monolauric acid ester (manufactured by Riken Vitamin Co., Ltd.; trade name "J-0021", HLB=16) as the polyglycerin fatty acid ester (B), 6.5 parts by weight of diglycerin monooleic acid ester (manufactured by Riken Vitamin Co., Ltd.; trade name "DO-100V", HLB=7.4) as the surfactant (C), and 5 parts by weight of distilled water were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

4.0 g of the obtained biologically active substance-containing water-solubilizing preparation was added into 100 mL of distilled water and uniformly diffused to obtain a biologically active substance-solubilized aqueous solution. The pH of this biologically active substance-solubilized aqueous solution was adjusted to 2.9 by the addition of a small amount of citric acid thereinto. Then, the resulting solution was heated until the internal temperature reached 95° C. to prepare an acid/heat-treated solution. The particle size distribution of the obtained acid/heat-treated solution was measured immediately after its preparation using a dynamic light scattering particle size distribution analyzer (manufactured by Horiba Ltd.; trade name "LB-550"). The analysis results are shown in Table 7.

TABLE 7

| Test agent used | Particle size distribution of acid/heat-treated solution (median size) (nm) |
| --- | --- |
| Water-solubilizing preparation of Example 27 | 33.8 |
| Water-solubilizing preparation of Example 28 | 65.7 |
| Water-solubilizing preparation of Example 29 | 32.0 |

Example 28

2.8 parts by weight of MCT was added to 1 part by weight of the ethanol extract of chrysanthemum flower obtained in Production Example 1 to prepare oil containing an ethanol extract of chrysanthemum flower.

20.5 parts by weight of the oil containing an ethanol extract of chrysanthemum flower as the oily ingredient (A) containing a biologically active substance and oil, 63 parts by weight of decaglycerin monolauric acid ester (manufactured by Riken Vitamin Co., Ltd.; trade name "J-0021", HLB=16) as the polyglycerin fatty acid ester (B), 6.5 parts by weight of diglycerin monooleic acid ester (manufactured by Riken Vitamin Co., Ltd.; trade name "DO-100V", HLB=7.4) as the surfactant (C), and 10 parts by weight of distilled water were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

4.0 g of the obtained biologically active substance-containing water-solubilizing preparation was added into 100 mL of distilled water and uniformly diffused to obtain a biologically active substance-solubilized aqueous solution. The pH of this biologically active substance-solubilized aqueous solution was adjusted to 2.9 by the addition of a small amount of citric acid thereinto. Then, the resulting solution was heated until the internal temperature reached 95° C. to prepare an acid/heat-treated solution. The particle size distribution of the obtained acid/heat-treated solution was measured immediately after its preparation using a dynamic light scattering particle size distribution analyzer (manufactured by Horiba Ltd.; trade name "LB-550"). The analysis results are shown in Table 7.

Example 29

2.8 parts by weight of MCT was added to 1 part by weight of the ethanol extract of chrysanthemum flower obtained in Production Example 1 to prepare oil containing an ethanol extract of chrysanthemum flower.

20.5 parts by weight of the oil containing an ethanol extract of chrysanthemum flower as the oily ingredient (A) containing a biologically active substance and oil, 73 parts by weight of decaglycerin monolauric acid ester (manufactured by Riken Vitamin Co., Ltd.; trade name "J-0021", HLB=16) as the polyglycerin fatty acid ester (B), and 6.5 parts by weight of diglycerin monooleic acid ester (manufactured by Riken Vitamin Co., Ltd.; trade name "DO-100V", HLB=7.4) as the surfactant (C) were each heated to 50° C. and uniformly mixed at 200 rpm under normal pressure using a stirrer (manufactured by AS ONE Corp.; trade name "Tornado PM202") to obtain a biologically active substance-containing water-solubilizing preparation.

4.0 g of the obtained biologically active substance-containing water-solubilizing preparation was added into 100 mL of distilled water and uniformly diffused to obtain a biologically active substance-solubilized aqueous solution. The pH of this biologically active substance-solubilized aqueous solution was adjusted to 2.9 by the addition of a small amount of citric acid thereinto. Then, the resulting solution was heated until the internal temperature reached 95° C. to prepare an acid/heat-treated solution. The particle size distribution of the obtained acid/heat-treated solution was measured immediately after its preparation using a dynamic light scattering particle size distribution analyzer (manufactured by Horiba Ltd.; trade name "LB-550"). The analysis results are shown in Table 7.

Example 30

The respective viscosities at varying temperatures of the biologically active substance-containing water-solubilizing preparations prepared in Examples 8, 25 to 27, and 29 were measured using Type-B Viscometer (MODEL: BL) manufactured by Tokimec Inc. The results are summarized in table 8.

TABLE 8

|  | Viscosity (cP) | | | |
| --- | --- | --- | --- | --- |
|  | 20° C. | 30° C. | 40° C. | 50° C. |
| Water-solubilizing preparation of Example 8 | 140100 | 53115 | 15090 | 8205 |
| Water-solubilizing preparation of Example 25 | 11440 | 6200 | 2375 | 1685 |
| Water-solubilizing preparation of Example 26 | 3605 | 2605 | 1390 | 910 |
| Water-solubilizing preparation of Example 29 | 53200 | 24475 | 11475 | 9600 |
| Water-solubilizing preparation of Example 27 | 9175 | 2938 | 4875 | 1750 |

All publications, patents, and patent applications cited herein are incorporated herein by reference in their entirety.

The invention claimed is:

1. A biologically active substance-containing water-solubilizing preparation comprising 1 to 50% by weight of an oily ingredient (A) containing a biologically active substance and medium-chain fatty acid triglyceride having 6 to 12 carbon atoms, 10 to 98% by weight of a polyglycerin fatty acid ester (B) having an HLB value of 12.5 or larger, 1 to 40% by weight of a surfactant (C) having an HLB value of 7 to 11.8.

2. The biologically active substance-containing water-solubilizing preparation according to claim 1, wherein the polyglycerin fatty acid ester (B) having an HLB value of 12.5 or larger is a polyglycerin monofatty acid ester comprising a polyglycerin having an average degree of polymerization of 10 and a fatty acid having 12 to 16 carbon atoms.

3. The biologically active substance-containing water-solubilizing preparation according to claim 1, wherein the surfactant (C) having an HLB value of 7 to 11.8 is a polyglycerin fatty acid ester comprising a polyglycerin having an average degree of polymerization of 2 to 6 and a fatty acid having 12 to 18 carbon atoms.

4. The biologically active substance-containing water-solubilizing preparation according to claim 1, wherein the biologically active substance is a plant extract, a fat-soluble vitamin, or a carotenoid.

5. The biologically active substance-containing water-solubilizing preparation according to claim 4, wherein the plant extract is an extract of one or more plants selected from the group consisting of licorice and *chrysanthemum* flower.

6. The biologically active substance-containing water-solubilizing preparation according to claim 1, further comprising water and/or an alcohol.

7. The biologically active substance-containing water-solubilizing preparation according to claim 6, wherein the alcohol is ethanol.

8. The biologically active substance-containing water-solubilizing preparation according to claim 6, wherein the total content of the water and the alcohol in the biologically active substance-containing water-solubilizing preparation is 12% by weight or less.

9. A biologically active substance-solubilized aqueous solution obtained by adding a biologically active substance-containing water-solubilizing preparation according to claim 1 to water or an aqueous solution.

10. The biologically active substance-containing water-solubilizing preparation according to claim 2, wherein the surfactant (C) having an HLB value of 7 to 11.8 is a polyglycerin fatty acid ester comprising a polyglycerin having an average degree of polymerization of 2 to 6 and a fatty acid having 12 to 18 carbon atoms.

11. The biologically active substance-containing water-solubilizing preparation according to claim 2, wherein the biologically active substance is a plant extract, a fat-soluble vitamin, or a carotenoid.

12. The biologically active substance-containing water-solubilizing preparation according to claim 3, wherein the biologically active substance is a plant extract, a fat-soluble vitamin, or a carotenoid.

13. The biologically active substance-containing water-solubilizing preparation according to claim 2, further comprising water and/or an alcohol.

14. The biologically active substance-containing water-solubilizing preparation according to claim 3, further comprising water and/or an alcohol.

15. The biologically active substance-containing water-solubilizing preparation according to claim 4, further comprising water and/or an alcohol.

16. The biologically active substance-containing water-solubilizing preparation according to claim 5, further comprising water and/or an alcohol.

17. The biologically active substance-containing water-solubilizing preparation according to claim 1, wherein the oily ingredient (A) is 1 to 40% by weight, the polyglycerin fatty acid ester (B) is 60 to 85% by weight, and the surfactant (C) is 3 to 10% by weight.

18. The biologically active substance-containing water-solubilizing preparation according to claim 1, wherein the surfactant (C) is diglycerin monooleic acid ester.

19. A method for producing a biologically active substance-solubilized aqueous solution, comprising adding a biologically active substance-containing water-solubilizing preparation to water or an aqueous solution to provide a mixture; and heat-treating and/or acid-treating the mixture, wherein the biologically active substance-containing water-solubilizing preparation comprises 1 to 50% by weight of an oily ingredient (A) containing a biologically active substance and medium-chain fatty acid triglyceride having 6 to 12 carbon atoms, 10 to 98% by weight of a polyglycerin fatty acid ester (B) having an HLB value of 12.5 or larger, and 1 to 40% by weight of a surfactant (C) having an HLB value of 7 to 11.8.

20. The method for producing a biologically active substance-solubilized aqueous solution according to claim 19, wherein the heat treatment comprises heating the mixture of the biologically active substance-containing water-solubilizing preparation and the water or the aqueous solution to 80° C. or higher.

21. The method for producing a biologically active substance-solubilized aqueous solution according to claim 19, wherein the acid treatment comprises adjusting the pH of the mixture of the biologically active substance-containing water-solubilizing preparation and the water or the aqueous solution to 4.0 or lower.

22. The method for producing a biologically active substance-solubilized aqueous solution according to claim 19, wherein the biologically active substance-containing water-solubilizing preparation used further comprises water and/or an alcohol.

* * * * *